United States Patent [19]

Caracciolo

[11] Patent Number: 4,588,381

[45] Date of Patent: May 13, 1986

[54] UNIVERSAL PIN FOR ORAL IMPLANTOPROSTHESIS

[76] Inventor: Francesco Caracciolo, Via Sangallo, 2, Milan, Italy

[21] Appl. No.: 550,572

[22] Filed: Nov. 10, 1983

[30] Foreign Application Priority Data

Jan. 14, 1983 [IT] Italy ................ 19104 A/83

[51] Int. Cl.$^4$ .............................................. A61C 8/00
[52] U.S. Cl. ................................................... 433/173
[58] Field of Search ............. 128/92 C, 92 CA, 92 B, 128/92 BC, 92 BA, 92 BB; 433/173, 174, 175, 176

[56] References Cited

U.S. PATENT DOCUMENTS

| | | | |
|---|---|---|---|
| 2,381,050 | 8/1945 | Hardinge | 128/92 BB |
| 2,699,774 | 1/1955 | Livingston | 128/92 BB |
| 3,576,074 | 4/1971 | Gault | 433/175 |
| 4,220,712 | 9/1980 | Staffalani | 433/173 |

Primary Examiner—Robert Peshock
Attorney, Agent, or Firm—Stevens, Davis, Miller & Mosher

[57] ABSTRACT

A new pin for oral implantoprosthesis is described which can be constructed in various forms, but in all cases is characterized by comprising two separate elements which are fitted together at the moment of the endo-osseous implantation. The pin when in its assembled form is characterized by comprising in its endo-osseous part two frusto-conical segments, namely an upwardly flared upper segment which provides for the retention of the pin in the compact bone region, and a downwardly flared lower segment which provides for retention of the pin in the cancellous bone region.

3 Claims, 16 Drawing Figures

FIG 4
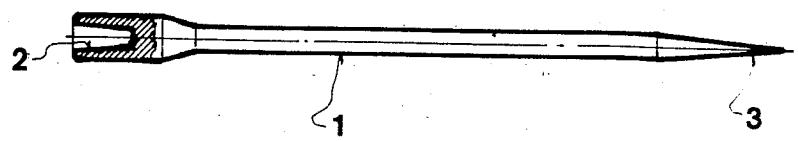
FIG 5
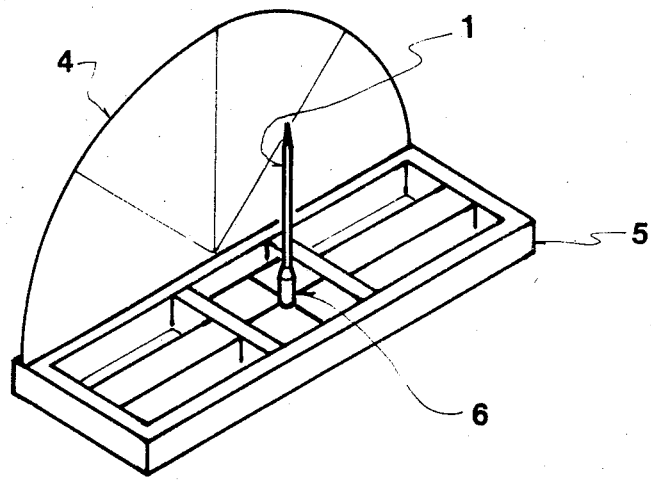
FIG 6A
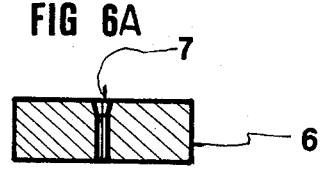
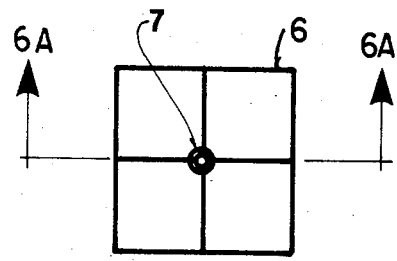
FIG. 6B

UNIVERSAL PIN FOR ORAL IMPLANTOPROSTHESIS

This invention relates to a universal pin for oral implantoprosthesis comprising an autonomous double-taper fixing system.

The new pin is defined as "universal" because it can be constructed in various sizes and dimensions, and completely replaces every missing dental element, for any variation in anatomy and for any person.

At the present time, oral implantology is directed essentially towards three types of implant, namely depth, extension and surface.

All these types of oral implant require highly specialised implantologists, of which there are few compared with requirements and with the number of dentists, lead to very high cost for the patient, and finally offer little reliability, particularly in the case of completely edentulous mouths.

In addition to these negative aspects which exist generally for any type of known implant, there are specific defects in each method, as follows:

DEPTH METHOD

This method comprises essentially
(a) endo-osseous spiral implants
(b) endo-osseous pin implants.

Endo-osseous spiral implants (a) are constituted essentially by hollow, solid or similar spiral elements having a length of 16 to 21 mm, and constructed of a suitable metal. These elements are implanted into the maxilla and/or mandible, and the dental prostheses are mounted thereon either by screwing or by pressure.

They have the following main drawbacks (Muratori: "L'implantologia orale multitipo", Publisher Castelli—Bologna 1972—pages 10, 50, 119): they necessarily require the support of natural teeth, and hence cannot be used for completely edentulous mouths; they must be fitted very deeply in order to create a lever arm which is very long relative to the external arm; the spiral has very little grip in the cancellous bone; the part emerging from the bone is reduced to a minimum (about 2 mm) for stability reasons, and consequently makes it very difficult to give the crown of the prosthesis the exact inclination for correct dental alignment; it is necessary to await the formation of the fibrous sleeve produced by the body for the implant to be able to adhere properly to the bone and to become fixed to it.

As this natural process requires several months, there is a long period in which the implant remains unstable and exposed to the danger of and damage deriving from infiltration.

Endo-osseous pin implants (b) are represented essentially by the Verbowsky pin, which is constituted by a head on which the prosthesis is fitted, a neck and a downwardly tapering body terminating in a point which is implanted into the bone. The body comprises a longitudinal slit in its central region, and a horizontal bore which inevitably weakens its structure.

Having made a hole in the alveolar bone, the pin is "fired" into its interior.

Theoretically, on implantation, the two parts into which the pin body is divided by the longitudinal slit should open outwards to anchor the pin to the bone, in a manner similar to the natural root. In practice, the sponginess of the bone does not allow anchoring in the proposed manner, and the pin remains unstable.

EXTENSION METHOD

This method consists essentially of implanting into the maxilla or mandible a strip having a length of some cm and of variable depth. One or more pins form an integral part of the strip, and emerge from the gingiva to allow fixing of the prosthesis. The main drawbacks of this method are firstly the difficulty, and indeed impossibility, of making in the bone a perfectly linear slot to which the strip can adhere with continuity; consequently, the implant is instable.

Again in this case, stability depends exclusively on the reconstitution of the osseous tissue. However, as stated the natural process requires several months, and during the whole of this time not only is the implant unstable, but is continuously exposed to the danger of infiltration and its effects.

SURFACE METHOD

This implantation method consists essentially of preparing for each case metal grids of special shape, for example in the shape of an "eight", from which the pin for the prosthesis emerges.

These grids are implanted horizontally into the bone by incising it only superficially; in this case, retention should be ensured essentially by the periosteum and gingiva.

The surface method, although not having the drawbacks of the extension method in which the bone is deeply incised, in no way ensures a secure and durable implantation. Moreover, the implantation must be carried out in two successive stages, which each time require the opening of the fibromucosa, with the imaginable negative effects deriving from the repeated intervention.

The applicant has now created, and forms the subject matter of the present invention, a pin for endo-osseous depth implantation which is arranged to constitute the basic element for anchoring fixed prosthesis, and in particular the autonomous pillar which, when fitted with a prosthetic crown, replaces any natural tooth.

It has characteristics which are totally different from any type of implantation element constructed up to the present time, and in particular any endo-osseous spiral or pin implantation element of known type. The new pin, as described in detail hereinafter, enables all the drawbacks of the previously known methods as summarised heretofore to be overcome.

The new pin for oral implantology according to the invention is characterised by being constituted by two separate elements, and, when assembled, by presenting in its lower endo-osseous part a particular structure which comprises two frusto-conical segments of opposing orientation, namely an upper pre-existing segment with its major base facing upwards, and a lower segment which is formed at the moment of assembly and has its major base facing downwards.

The assembly of this double-taper structure ensures perfect retention of the pin in the bone, independently of the reconstitution of the bone tissue, and further ensures an absolutely autonomous implantation, i.e. without support by the natural teeth being necessary.

The application of the pin is also very simple, as it requires only very limited drilling of the bone, which is carried out in a single sitting.

The invention will be more apparent from the description given hereinafter of two possible embodiments thereof.

BRIEF DESCRIPTION OF THE DRAWINGS

FIGS. 4, 5, 6a and 6b show the device for giving the pin the required inclination;

Figure 1A:
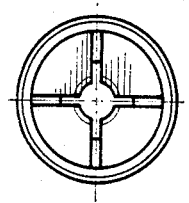
FIG. 1a is a view toward the bottom of FIG. 1b.
Figure 1B:
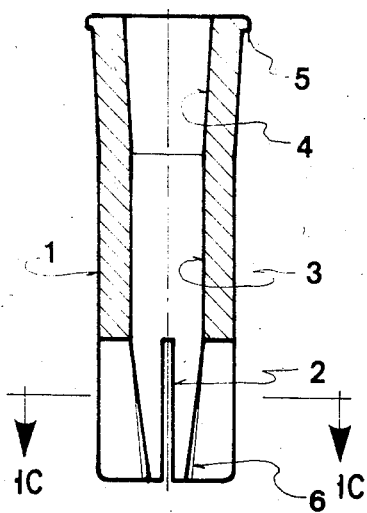
FIG. 1b is a longitudinal sectional view.
Figure 1C:
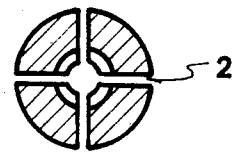
FIG. 1c is a sectional view taken on the arrowheaded line of FIG. 1b.

The first embodiment of the pin is illustrated on the first drawing, which comprises FIGS. 1, 2 and 3. The other embodiment is illustrated on the third drawing, which comprises 7, 8 and 9.

The illustrated pins are constructed of titanium alloy and in various sizes. They can however be constructed of different metals or metal alloys.

Figure 2A:
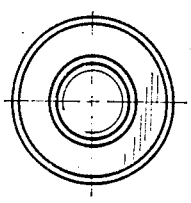
FIG. 2a is a view toward the bottom of FIG. 2b.
Figure 2B:
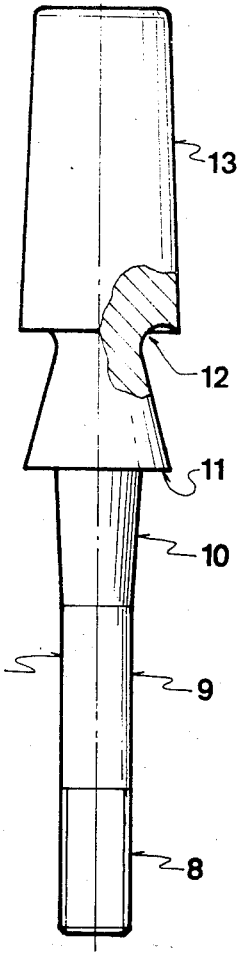
FIG. 2b is a side elevation, partly in section, of the solid element.

The pin illustrated on the first drawing comprises a hollow element 1, which is shown in FIG. 1a as a view from below and as a central longitudinal section in FIG. 1b, and a solid element 7 which is shown in FIG. 2a as a view from below and in FIG. 2b as a partly sectional side view.

Figure 3A:
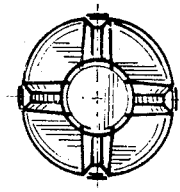
FIG. 3a is a view from below of FIG. 3b.
Figure 3B:
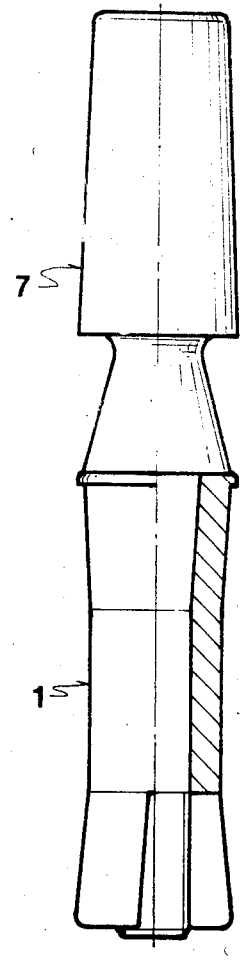
FIG. 3b is a side elevation, partly in section, of the element of FIGS. 1b and 2b assembled together.

FIG. 3a shows a view from below and in FIG. 3b a partly sectional side view of the pin in its final assembled state, resulting from fitting the element 1 and the element 7 together.

The following functionally separate parts are visible in the hollow element 1: an upwardly flared frusto-conical upper part 4, in which the outer wall and inner wall can have equal or different inclination; a cylindrical central part 3 with its outer wall and inner wall parallel; and a lower part 6 with its outer cylindrical wall of diameter equal to the diameter of the central part, and with its inner wall narrowing downwards to form a smooth or threaded taper.

The lower part 6 comprises two through slots 2 which are orthogonal to each other, and are shown in detail at the foot of FIG. 1.

On its upper part 4, the element 1 comprises a projecting rim 5.

With particular reference to FIG. 2, the following functionally separate parts are visible in the solid element 7, which is inserted into the hollow part of the element 1: a frusto-conical upper part or head 13 which has its major base at the bottom, and which projects from the gingiva in order to support the prosthesis; a frusto-conical central part or neck 11 with its major base at the bottom and having a cavity 12 worked into its upper part as shown in the figure; and a lower part or body in which three segments can be distinguished, namely an upper frusto-conical segment 10 with its outer profile exactly corresponding to the inner profile 4 of the element 1 with which it has to mate perfectly, a central cylindrical part 9 of diameter such as to enable it to be perfectly inserted in a sealed manner into the central part 3 of the element 1, and a terminal part 8 which can be a simple extension identical to the part 9 or can be threaded to correspond to a possible thread on the terminal part 6 of the element 1 into which it is to be inserted and to project below it by a few tenths of a millimeter.

The new pin according to the present invention is fitted as follows:

(a) the gingiva is incised, and a hole is made in the maxilla or mandible with a diameter equal to the diameter of the central part 3 of the element 1. The element 1 is pressed into this hole so that the rim 5 rests by its lower part on the bone, and seals against it to prevent any possibility of infiltration.

(b) the element 7 is introduced into the element 1, and its lower part 8 is forced into the lower part 6 of the element 1 either by simple vertical pressure if the facing walls are smooth, or by screwing if they are threaded. By means of this operation, the four parts into which the segment 6 is divided are forced outwards, and the profile of this latter segment is changed from cylindrical to downwardly flared frusto-conical.

In its final state, which is clearly visible in FIG. 3, the new pin thus comprises two tapers in the endo-osseous part which open in opposite directions to create solid fixing both in the compact bone region and in the cancellous bone region. The pin also comprises a slight rim 5 which "closes" on to the bone, and a slight groove 12 which "closes" on to the gingiva. The terminal part 13 emerges completely, and constitutes the absolutely stable and secure connection point for the prosthesis.

Figure 7:
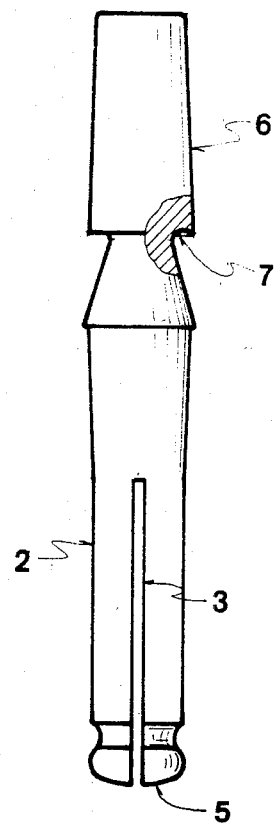
FIGS. 7 and 8 are side views, partly in section, of the upper element of a second embodiment.
Figure 8:
Figure 9:
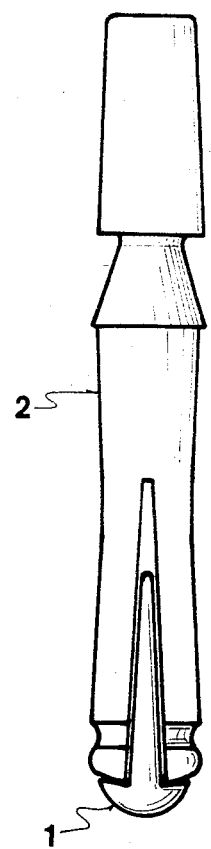
FIG. 9 is a side view of assembly of the upper and lower elements.

The second embodiment of the new universal pin according to the invention is shown in FIGS. 7, 8 and 9.

Figure 10:
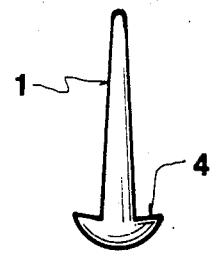
FIGS. 10 and 11 are front and side views of the lower element.
Figure 11:
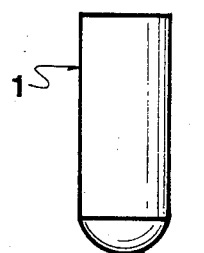

With particular reference to FIGS. 7 and 10, it can be seen that in this case the two constituent elements of the double-taper pin are the following:

a first base element 1 constituted by a wedge of trapezoidal cross-section terminating in a rounded base part in the form of a spherical cap 4 (this element is shown in frontal view in FIG. 10 and side view in FIG. 11); and a second element 2, comprising three segments with different functions, namely a head 6 of frusto-conical structure forming the part which emerges the gingiva and creates the support for the prosthesis, a neck which is also of frusto-conical structure and is connected to the head by a groove 7 which ensures perfect "closure" on to the gingiva, and the actual body which comprises an upper part having a frusto-conical structure which is inverted relative to that of the neck and slightly withdrawn from it in such a manner as to leave a rim which rests on the bone to form a "seal" thereon, and a lower cylindrical part which is traversed over its entire length by a slot of such a width as to allow insertion of the element 1.

The new pin is clearly visible in its final state in FIG. 9, from which it can be seen that mounting the second element over the first causes the lower part of the element 2 to widen outwards and to create a terminal frusto-conical structure which together with that existing in the upper part of the body forms the double taper which is characteristic of the new pin, and which ensures absolute stability and rigidity of the osseous implantation.

The pin is fitted in the following manner:

the gingiva is incised, and a hole of diameter equal to that of the pin is made in the bone. The two elements 1 and 2, previously coupled to each other by simple contact, are introduced together into this hole. The pin is then inserted until it touches the bottom of the hole.

This operation causes the two parts into which the slot 3 divides the lower part of the element 2 to widen outwards, and thus to form the second taper of oval cross-section which together with the first, which is of circular cross-section and is already present in the upper part of the body of the element 2, provides absolutely stable fixing of the pin to the bone.

The new pin, both in the embodiment shown in FIG. 3 and in the embodiment shown in FIG. 9, can comprise in its lower part a groove as shown at the point 5 of FIG. 7. Such a groove further enhances the fixing of the pin to the bone, with the formation in its interior of new fibrous or osseous tissues.

It is apparent that modifications and improvements can be made to the new pin, without leaving the scope of the claimed invention.

The table reproduced hereinafter by way of example gives the characteristic measurements of some pins of the type illustrated in FIGS. 1, 2 and 3.

The numerical symbols used for identifying the various pins indicate the ratio of the length in millimeters of the first element 1 to the length in millimeters of the second element 7.

It is not essential for the various parts of the pin to be of circular cross-section, in that equally good results are obtained by making the parts with inner or outer polygonal cross-sections.

Because of the optimum dimensions both of the emerging part and of the endo-osseous part, the applicant has found that it is possible to give the pin, in a simple and precise manner, the most suitable inclination to enable the prosthesis fixed thereon to be inserted perfectly between the natural teeth, or to replace them totally, thus providing prostheses which are perfect both from the functional and appearance aspects.

The device used by the applicant for giving the pin the required inclination is shown in FIGS. 4, 5 and 6.

Said device consists essentially of a rectangular frame 5 which, by way of example, has a major side of 30–35 cm on a minor side of 10–15 cm. Along one of the major sides a slot is formed into which a goniometer 4 is inserted in a plane perpendicular to the plane of the frame, the goniometer having a centrally indicated zero, and arc measurements decreasing from the outside towards the zero indicated on the two lateral circle quarters.

Adjacent to the major side which lies opposite the side into which the goniometer is inserted, there is disposed, aligned with the base centre of the goniometer, a

TABLE

| | Models and Dimensions | | | | | |
|---|---|---|---|---|---|---|
| | 7/17 | | 10/20 | | 14/24 | |
| PIN ELEMENTS AND NOMENCLATURE OF PARTS | Total & partial heights mm | Diameter at points indicated mm | Total & partial heights mm | Diameter at points indicated mm | Total & partial heights mm | Diameter at points indicated mm |
| 1st ELEMENT (1) | 7.0 | | 10.0 | | 14.0 | |
| Upper part (4) | 3.0 | | 3.0 | | 3.0 | |
| Safety ring (stop) (5) | 0.3 | | 0.3 | | 0.3 | |
| point of support of 2nd outer element | | 3.3 | | 3.3 | | 3.3 |
| point of support at outer bone | | 3.5 | | 3.5 | | 3.5 |
| upper point of outer taper | | 3.2 | | 3.2 | | 3.2 |
| Outer taper | 2.7 | | 2.7 | | 2.7 | |
| upper | | 3.2 | | 3.2 | | 3.2 |
| lower | | 3.0 | | 3.0 | | 3.0 |
| Inner taper | 3.0 | | 3.0 | | 3.0 | |
| upper | | 1.9 | | 1.9 | | 1.9 |
| lower | | 1.6 | | 1.6 | | 1.6 |
| Central part (3) | 1.0 | | 4.0 | | 8.0 | |
| outer | | 3.0 | | 3.0 | | 3.0 |
| inner | | 1.6 | | 1.6 | | 1.6 |
| Lower part (2) | 3.0 | | 3.0 | | 3.0 | |
| Outer | | 3.0 | | 3.0 | | 3.0 |
| Inner taper (threaded or not) | 3.0 | | 3.0 | | 3.0 | |
| upper | | 1.6 | | 1.6 | | 1.6 |
| lower | | 0.8 | | 0.8 | | 0.8 |
| "Nascent" taper | 3.0 | | 3.0 | | 3.0 | |
| outer upper | | 3.0 | | 3.0 | | 3.0 |
| outer lower | | 3.8 | | 3.8 | | 3.8 |
| inner upper and lower | | 1.6 | | 1.6 | | 1.6 |
| 2nd ELEMENT (7) | 17.2 | | 20.2 | | 24.2 | |
| Frusto-conical head (13) | 7.0 | | 7.0 | | 7.0 | |
| upper | | 3.0 | | 3.0 | | 3.0 |
| lower | | 3.3 | | 3.3 | | 3.3 |
| Irregularly concave neck (11-12) | 3.0 | | 3.0 | | 3.0 | |
| upper | | 2 | | 2 | | 2 |
| lower | | 3.3 | | 3.3 | | 3.3 |
| Body | | | | | | |
| Upper part (10) | 7.2 | | 10.2 | | 14.2 | |
| Taper | 3.0 | | 3.0 | | 3.0 | |
| upper | | 1.9 | | 1.9 | | 1.9 |
| lower | | 1.6 | | 1.6 | | 1.6 |
| Central cylindrical part (9) | 1.0 | 1.6 | 4.0 | 1.6 | 8.0 | 1.6 |
| Lower part (threaded or not) (8) | 3.2 | 1.6 | 3.2 | 1.6 | 3.2 | 1.6 | block 6 into which there is centrally inserted, and thus aligned with the goniometer zero marking, a sheath 7 which is arranged to receive the second pin element according to the invention, over its entire height. The neck and element head 8 emerge from this sheath, and the head 8 can be inserted into the socket head 2 of the lever 1, by means of which the element head can be given the required inclination by adjusting it with reference to the graduated goniometer dial.

The element head 7 is preferably given two inclinations at 90° apart, one corresponding to inclination in the mesio-distal direction and the other corresponding to inclination in the vestibulo-lingual direction of the natural teeth. In this manner, it is possible to obtain best possible mastication, phonation and appearance when the prosthesis is fixed to the pin.

Summarising, the new universal pin for oral implantoprosthesis, comprising an autonomous double-taper fixing system, according to the invention, has the following characteristics, all of which represent advantageous aspects of the invention:

a first upper taper which creates a solid point of fixing in the compact bone, in line with the periosteum a second lower taper which arises on fitting together the two component parts of the pin, to create a second very solid point of fixing in the cancellous bone. As this second taper has a maximum diameter greater than that of the upper taper, any linear movement of the pin along its vertical or horizontal axes or any rotation about said axes is prevented it requires no external supports nor cementing, and constitutes an autonomous support to which any prosthesis can be fixed it can be constructed in a large range of sizes, including very small, which enables it to be inserted into any point of the mandible or maxilla it does not require reconstitution of the bone in order to become stable it does not require special instruments for its implantation. The normal drill together with a number of graduated spiral drill bits are sufficient to create the holes of the necessary depth when fitted with the appropriate prosthesis crown, the pin can support considerable stress, even exceeding that to which a tooth is normally subjected.

Numerous modifications can be made to the pin according to the invention, all lying within the scope of the following claims.

What is claimed is:

1. A pin for oral implantoprosthesis comprising:
a first element for insertion into a hole in the bone of a patient, said first element having an elongated cylindrical body with an opening extending axially therethrough, the opening having three parts;
an upper part in which the inner and outer walls are inclined to define a frusto-conical upwardly facing interior;
a center cylindrical part in which the inner and outer walls are parallel and a lower part which is externally cylindrical and internally conical with at least two axially extending slots dividing the lower part into at least two portions which can be spread mutually apart;
a second element having a lower portion for insertion into the opening of said first element and an upper portion for insertion into the prosthesis, said lower portion having three parts corresponding to the three parts of the opening with an upper part having a frusto-conical exterior of a size and shape to mate precisely with the corresponding part of the opening, a central cylindrical part of a size and shape to mate precisely with the central cylindrical part of the opening and a lower part which is of a size and shape to engage the internally conical surface of the opening and force the walls thereof radially outwardly to deform the externally cylindrical lower part of the first element into an outwardly tapered shape when the lower portion of the second element is inserted into the opening of the first element.

2. The pin of claim 1 in which the first element has an upper rim arranged to rest on the bone in which the first element is inserted to form a seal therewith.

3. The pin of claim 1 in which the second element has a neck portion with a groove having a concave cross-section, said neck being slightly above its juncture with the first element.

* * * * *